United States Patent
Agarwal et al.

(10) Patent No.: US 12,186,450 B2
(45) Date of Patent: Jan. 7, 2025

(54) COMPOSITION OF SUBSTANTIALLY SPHERICAL GRANULE FOR BONE REGENERATION

(71) Applicant: OSTEONOVUS LLC, Toledo, OH (US)

(72) Inventors: Anand Agarwal, Ottawa Hills, OH (US); Xiaodong Gao, Ann Arbor, MI (US); Smruti Gore, Toledo, OH (US)

(73) Assignee: OSTEONOVUS LLC, Toledo, OH (US)

( * ) Notice: Subject to any disclaimer, the term of this patent is extended or adjusted under 35 U.S.C. 154(b) by 8 days.

(21) Appl. No.: 17/845,168

(22) Filed: Jun. 21, 2022

(65) Prior Publication Data
US 2022/0401620 A1 Dec. 22, 2022

Related U.S. Application Data

(60) Provisional application No. 63/212,917, filed on Jun. 21, 2021.

(51) Int. Cl.
*A61L 27/32* (2006.01)
*A61L 27/10* (2006.01)
(Continued)

(52) U.S. Cl.
CPC .............. *A61L 27/32* (2013.01); *A61L 27/10* (2013.01); *A61L 27/12* (2013.01); *A61L 27/306* (2013.01);
(Continued)

(58) Field of Classification Search
CPC .......... A61L 27/32; A61L 27/10; A61L 27/12; A61L 27/306; A61L 27/52; A61L 27/54;
(Continued)

(56) References Cited

U.S. PATENT DOCUMENTS

| 5,512,094 A | 4/1996 | Linton |
| 6,495,257 B1 | 12/2002 | Terase et al. |

(Continued)

FOREIGN PATENT DOCUMENTS

WO    WO-2017165612 A1 *  9/2017    .......... A61L 24/0015

OTHER PUBLICATIONS

Nabiyouni, Maryam, et al. "Magnesium-based bioceramics in orthopedic applications." Acta biomaterialia 66 (2018): 23-43. (Year: 2018).*

(Continued)

*Primary Examiner* — Isaac Shomer
*Assistant Examiner* — Bryan James Rego
(74) *Attorney, Agent, or Firm* — Jacob M. Ward; Ward Law Office LLC (57) ABSTRACT

A composition for bone regeneration includes substantially spherical granules. Each of the spherical granules include an outer shell including magnesium phosphate and nano-sized silica and a bioactive core encapsulated by the outer shell. The granules include macro-pores and micro-pores. The macro-pores are intergranular spaces between adjacent granules, and the micro-pores are intragranular nanopores formed on the outer shell of each of the granules. A method of producing the substantially spherical granules, includes providing a mixture of a biological active powder, magnesium phosphate, and an initiator with a colloidal silica solution; rotating the mixture with dual asymmetric centrifugation for a predetermined amount of time; and drying the resulting material.

9 Claims, 4 Drawing Sheets

(51) Int. Cl.
  *A61L 27/12* (2006.01)
  *A61L 27/30* (2006.01)
  *A61L 27/52* (2006.01)
  *A61L 27/54* (2006.01)
  *A61L 27/56* (2006.01)

(52) U.S. Cl.
  CPC ............... *A61L 27/52* (2013.01); *A61L 27/54* (2013.01); *A61L 27/56* (2013.01); *A61L 2430/02* (2013.01)

(58) Field of Classification Search
  CPC .... A61L 27/56; A61L 2430/02; A61L 27/025; A61L 27/446; A61L 27/46
  USPC ......................................................... 424/423
  See application file for complete search history.

(56) References Cited

U.S. PATENT DOCUMENTS

| | | | |
|---|---|---|---|
| 9,192,914 | B2 | 11/2015 | Miyahara et al. |
| 9,205,035 | B2 | 12/2015 | Engqvist et al. |
| 9,234,104 | B2 | 1/2016 | Michos et al. |
| 11,241,515 | B2 | 2/2022 | Schlossberg et al. |
| 2008/0248086 | A1* | 10/2008 | Asgari .................... A61L 27/58 |
| | | | 424/426 |
| 2015/0005392 | A1 | 1/2015 | Bhaduri et al. |
| 2019/0099515 | A1* | 4/2019 | Bagga .................... A61L 27/56 |

OTHER PUBLICATIONS

Written Opinion of the International Searching Authority dated Oct. 27, 2022.

\* cited by examiner

COMPOSITION OF SUBSTANTIALLY SPHERICAL GRANULE FOR BONE REGENERATION

CROSS-REFERENCE TO RELATED APPLICATIONS

This application claims the benefit of U.S. Provisional Application No. 63/212,917, filed on Jun. 21, 2021. The entire disclosure of the above application is incorporated herein by reference.

FIELD

The present technology relates to compositions for bone regeneration, and more particularly to compositions containing spherical granules for bone regeneration.

INTRODUCTION

This section provides background information related to the present disclosure which is not necessarily prior art.

Synthetic bone graft substitute refers to the bone graft materials consisting only of materials that are synthesized via chemical reactions; these grafts contain no cell, tissue, protein, or other substances obtained from humans or animals. Calcium phosphate is a major type of material used for synthetic bone graft products.

Osteoconductive synthetic bone graft materials must allow fibroblastic or mesenchymal stem cells to attach on their surfaces, followed by proliferation, differentiation and other cellular activities. Where the cells stay, there will be bone formation. Therefore, the physical characteristics of synthetic bone graft need to be well designed so that the cells can stay at desired sites.

In general, there are two different designs for synthetic bone graft surfaces, leading to two different bone formation patterns. The first design is to have a strong bone graft mass with limited to no pores. The mass normally can have certain mechanical strength to augment bone tissue around it, but new bone formation only happens on the outside of the mass, and slowly grows onto the mass upon resorption/shrinkage of the bone graft. The second design is to have many small bone graft mass randomly packed together; they are called granules. The granules cannot provide mechanical support to bone tissue, however, the granular form results in much more bone graft surfaces. The random packing inevitably forms inter-granular channels and pores in between, which allows the cells to come close to the granule surfaces, followed by attachment and proliferation. New bone formation around a structure like this will have new bone tissue ranging from sites near the granule surfaces all the way to the center of the packed granules. Bone healing is much faster in the second design.

Production of spherical granules can be challenging, especially for bioactive ceramic materials. Normally, the formation of spherical granules made from ceramic involves molding, heating, grinding, and/or milling. High-temperature heating (1000° C.) is almost inevitable in the processes, since the formation of granules that are larger enough for the application of bone graft products requires fusion or melt of many small ceramic particles, which are normally obtained as precursors from chemical reactions. The disadvantage of high temperature heating process is the energy can often alter the crystal structure of ceramic, resulting in phase transition. Also, high temperature offers a lot of kinetic mobility to atoms and ions, leading to fusion of particles, eventually particle surfaces are smooth and few intragranular pores can exist. These physical features are not favorable for cells to attach and proliferate compared to rough and porous surfaces. Additional measures have to be taken to enhance the bioactivity of such materials.

Accordingly, there is a continuing need for more efficient methods of producing spherical particles.

SUMMARY

In concordance with the instant disclosure, more efficient methods of producing spherical particles, have surprisingly been discovered.

The spherical granules of the present disclosure can advantageously be created under low temperature (<150° C.) using ceramic powders. Such composition has evenly distributed intergranular pores, rough granule surfaces and micropores in nanometers within each granule.

In one embodiment, a composition for bone regeneration includes substantially spherical granules. Each of the spherical granules include an outer shell including magnesium phosphate and nano-sized silica and a bioactive core encapsulated by the outer shell. The granules include macro-pores and micro-pores. The macro-pores are intergranular spaces between adjacent granules, and the micro-pores are intragranular nanopores formed on the outer shell of each of the granules.

In another embodiment, a method of producing the substantially spherical granules, includes providing a mixture of a biological active powder, magnesium phosphate, and an initiator with a colloidal silica solution; rotating the mixture with dual asymmetric centrifugation for a predetermined amount of time; and drying the resulting material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

All documents, including patents, patent applications, and scientific literature cited in this detailed description are incorporated herein by reference, unless otherwise expressly indicated. Where any conflict or ambiguity can exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that can be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter can define endpoints for a range of values that can be claimed for the parameter. For example, if Parameter X is exemplified herein to have value A and also exemplified to have value Z, it is envisioned that Parameter X can have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X can have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it can be directly on, engaged, connected or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Methods of making and compositions for bone tissue regeneration are disclosed. The composition can include substantially spherical granules. The term "substantially spherical" as used herein is intended to describe a particle whose shape is nearly or mostly spherical, but which can nonetheless not have an identical radius at all points. In other words, substantially spherical particles cannot be perfectly spherical. Embodiments of spherical granules for bone tissue regeneration are also disclosed.

The present disclosure contemplates a composition for bone regeneration. The composition can be suitable for orthopedic implantation to facilitate bone healing process, as described in greater detail, herein. Further, the composition can be suitable for any additional uses, known to those of skill in the art, wherein the facilitation of bone growth is desirous. The composition can include substantially spherical granules. Each of the substantially spherical granules can include an outer shell and a bioactive core. The bioactive core can be substantially or completely encapsulated by the outer shell.

The outer shell can include magnesium phosphate and silica. The silica can be a nano-silicon provided as a colloidal $SiO_2$ aqueous solution or any alternative silica compound or solution known to those of skill in the art for being functional in the present composition. The $SiO_2$ nanoparticles can be used to increase a surface area of the granules due to the high surface-to-volume ratio of the nanoparticles. This high surface-to-volume ratio of the nanoparticles benefits cell accommodation because the additional surface area can encourage additional cell growth.

The presence of $Mg^{2+}$ is beneficial for new bone formation by enhancing cell accommodation and differentiation. Magnesium phosphate-based cements (MPC) exhibit good biocompatibility, and an absence of inflammatory reactions, formation of fibrous tissue and toxicity, when tested in vivo. The dissolution rates of several magnesium phosphate compounds are higher than that of certain calcium-based cements. Therefore, magnesium phosphate with the beneficial biocompatibility, biological properties, and biodegradability is preferably used in the composition of the present invention.

In certain embodiments, the magnesium phosphate can be present as a powder. The magnesium phosphate composition can include, but are not limited to, a powder of $MgHPO_4$, $MgHPO_4 \cdot xH_2O$, $Mg_3(PO_4)_2$, $Mg_3(PO_4)_2 \cdot xH_2O$, or combinations thereof. A skilled artisan can select other suitable magnesium phosphate compounds, as desired.

The outer shell can also include additional filler or other compatible compositions as are known to those of skill in the art without departing from the spirit of the present invention.

The bioactive core can include calcium phosphate, a bioactive glass, and combinations thereof. Calcium phosphate (CaP) is a general name for a family of inorganic salts that contain calcium cations and orthophosphate, metaphosphate, or pyrophosphate anions. The calcium phosphate compounds used for the composition can include, but are not limited to, hydroxyapatite (HA), β-tricalcium phosphate (β-TCP), including dicalcium phosphate anhydrous (DCPA), α-tricalcium phosphate, octacalcium phosphate, dicalcium phosphate dihydrate, amorphous calcium phosphate, other calcium phosphate compounds known to those of skill in the art, and the combinations thereof. These calcium phosphate compounds can be used to provide an improved healing response and higher resorption rate than other HA-based materials.

Hydroxyapatite is a major constituent of human bone and enamel and human hard tissue. HA is biocompatible, osseointegrative, and osteoconductive, which makes it an excellent candidate as a bone graft material. Tricalcium phosphate has much higher solubility than HA (theoretical solubility is about 100 times higher than HA) and converts quickly into HA under physiological conditions.

Compositions that include both HA and β-TCP can be synergistic. The combination can be more bioactive due to the presence of β-TCP, and the stability of the graft is controlled because of the presence of HA. The ratio of HA:β-TCP can range from 60:40 to 10:90 depending on the composition. The ratio can be adjusted by one of skill in the art based on the specific use of the composition.

Additionally, it was unexpectedly found that the incorporation of magnesium phosphate in a calcium phosphate composition can improve the degradation kinetics of the composition in vivo, as compared to that of a calcium phosphate composition alone. Thus, the incorporation of a magnesium phosphate outer shell can help improve the degradation kinetics for the calcium phosphate core.

The outer shell of the generally spherical granules can have a textured surface. The surface texture of the granules can be formed by a combination of the plurality of granules. There can be macro-pores, which can be intergranular spaces between adjacent granules. There can also be micro-pores, which can be intragranular nanopores formed on the outer shell of each of the granules. The micro-pores can be either uniformly shaped or irregularly shaped. The micro-pores can allow cells, fluid, or tissues to infiltrate into the center of the packed granules thereby further encouraging bone growth.

The biologically active glass, for use in the core, can include any silica based composition that is biologically active. These compositions can include silica based compounds with multiple metal/non-metal oxides which render the compound "bioactive." This type of material can form an apatite layer on their surfaces when present in a body fluid. This characteristic can enable the composition to directly bond to natural bone, thereby rending the composition "biologically active."

When bioactive glass is in the presence of magnesium phosphate and colloidal silica solution, the bioactive glass can be encapsulated. Advantageously, the resultant composition can include numerous particles of different compositions, in which bioactive glass has low degradability and other components/compositions contained therein can have a higher degradability. After implantation into a body, the portion with high degradability can help provide short-term healing, whereas the bioactive glass that is only slowly degraded can help provide a stable scaffold for bone formation after the highly degradable portion is completely degraded. Additionally, encapsulation of bioactive glass with magnesium phosphate and nano-sized silica can preserve the chemical structures of each individual component, as well as any biological properties related thereto.

Examples of bioactive glass can include, but are not limited to, 45S5 (46.1 mol % $SiO_2$, 24.4 mol % $Na_2O$, 26.9 mol % CaO and 2.6 mol % $P_2O_5$), S53P4 (53.8 mol % $SiO_2$, 21.8 mol % CaO, 22.7 mol % $Na_2O$ and 1.7 mol % $P_2O_5$), 13-93 (54.6% $SiO_2$, 22.1% CaO, 7.9% $K_2O$, 7.7% MgO, 6.0% $Na_2O$, and 1.7% $P_2O_5$), 58S (60 mol % $SiO2$, 36 mol % CaO, 4 mol % P2O5), 68S (70 mol % $SiO_2$, 26 mol % CaO, 4 mol % $P_2O_5$), 63S (63 mol % $SiO_2$, 28 mol % CaO, 9 mol % $P_2O_5$), 77S (80 mol. % $SiO_2$, 16 mol. % CaO, 4 mol. % $P_2O_5$), 80S (80 mol % $SiO_2$, 15 mol % CaO, 5 mol % P2O5), 35SM (35 mol % SiO2, 50 mol % CaO, 7 mol % P2O5, 7 mol % MgO, 1 mol % $CaF_2$), 85S (85 mol % SiO2, 10 mol % CaO, 5 mol % $P_2O_5$), 70S30C (70 mol % SiO2, 30 mol % CaO), and combinations thereof.

The outer shell of the substantially spherical granule can be also used to encapsulate additional substances. In other words, the outer shell can be used as a micro-encapsulation substance. Some non-limiting examples of substances that can be encapsulated or micro-encapsulated include, but are not limited to, antibiotics, stem cells, and peptides. These substances can be used to support the bone healing ability of the composition. Therefore, these substances can become part of the bone graft composition's substantially spherical granules. In certain embodiments, additional substances, such as peptides, growth factors, antibiotics, can also be micro-capsulated within the substantially spherical granules. Advantageously, this micro-capsulation can militate against early degradation of the encapsulated material.

In a specific embodiment, the composition can be mixed with a carrier that can be used for implantation of the composition. A non-limiting example of such a carrier is a water soluble biopolymer. Examples of such biopolymers include, but are not limited to, cellulose, chitosan, alginate, and other similar biopolymers known to those of skill in the art. These biopolymers be hydrated, thereby forming a hydrogel. The hydrogel can include one of a biopolymer, a protein, a gum, a carbohydrate, and a cellulose, as non-limiting examples. More particularly, the hydrogel can include biopolymers, proteins (e.g., gelatin, pectin), gums (e.g., agar, sodium alginate), carbohydrates (e.g. starch, chitosan), and celluloses (e.g. carboxymethylcellulose, methylcellulose), to form the hydrogel or putty, which can be used to wrap the substantially spherical granules of the composition to form a putty-like bone graft. The putty can also be adhesive to bone tissue and can therefore remain in place and conform to the surfaces of bone tissue onto which it is placed. These nano silica particles of the substantially spherical granules can also interact with the biopolymer molecules to further aid in maintaining the integrity of the biopolymer gels. Further, if a more aqueous solution is used, the polymer gels will not easily fall apart due to the lavage created by the substantially spherical granules of the composition.

Surgeries involving biomaterials such as synthetic bone graft materials can have a high risk of developing infections due to adhesion of the bacteria to the biomaterials and production of a biofilm from the bacterial strains. This can militate against infection and aid in wound healing. Therefore, the use of a composition loaded with antibiotics into the surgical site can be useful to tackle this problem.

In a specific embodiment, the hydrogel can further include at least one therapeutic component. Examples of such therapeutic components include, but are not limited to, antibiotic drugs, vancomycin, tobramycin, or gentamycin, as non-limiting examples. The antibiotic drugs can be produced in hydrophilic forms, so they can easily be mixed with biopolymers in hydrophilic forms. When the therapeutic drugs are mixed with the polymer gels, they can interact with each other at molecular level, such that after implantation, and upon the degradation of the polymer gels, the drugs can be gradually be released to the body. These antibiotics can also be micro-capsulated to help increase stability and improve handling and to create a controlled release of the drug. Additionally, after the degradation of the hydrogel the spherical granules can function as a scaffold for osteoconductive healing.

It should be appreciated that the composition can be included in alternative forms, which are not limited to hydrogel embodiments of the composition disclosed above. A skilled artisan can provide the composition in any suitable form, as desired. One example includes, but is not limited to, mixing the substantially spherical granules with bone cement for use in osteomyelitis treatment. The release of the drugs can then be dependent and/or reliant upon on the degradation of the bone cement.

The composition of the present disclosure can also include micro-encapsulated substances that can support bone healing. Micro-capsulation refers to a technique that can produce small spherical particles with diameters ranging from 1 to 1000 μm. These can be produced using natural or synthetic polymeric materials or inorganic materials. Solid or porous microcapsules can be obtained for specific intended applications. The microcapsules can contain various substances based on the intended application. The materials for the micro-capsulation can be polymeric materials, including but not limit to gelatin, polyvinyl alcohol, ethyl cellulose, cellulose acetate phthalate and styrene maleic anhydride, or directly with the claimed composition herein. The various micro-capsulation processes can be divided into chemical, physiochemical, and electrostatic and mechanical processes. Chemical processes include the interfacial and in situ polymerization methods. Physiochemical processes include coacervation phase separation, complex emulsion, meltable dispersion and powder bed methods. Mechanical processes include the air-suspension method, pan coating, and spray drying, spray congealing methods. The micro-capsulated substances such as antibiotics, peptides, or stem cells can be mixed with the bone graft composition granules disclosed herein for producing a mixture for implantation. The encapsulated substances can dissolve when in contact with biological fluids such as blood, releasing and dispersing the substances within. The dissolving rate for these can depend on the specific encapsulation, the nature of the biopolymer or other carrier that is used for implantation of the composition in the body, and the nature of the specific substance. It should be appreciated that when stem cells are mixed in the composition, nano-peptides can also be added to support the viability of the stem cells.

The composition of the present disclosure can also include macro-encapsulated substances that can support bone healing, such as peptides, stem cells, growth factors, antibiotics. Macro-capsulation refers to a range of techniques used to enclose medicines in a stable shell forming a capsule that has a size of several millimeters to centimeters, allowing them to, for example, be taken orally or be surgically implanted/packed into a suitable void. This technique can be used to capsulate the bone graft composition claimed herein. Hard-shelled capsules, which contain dry, powdered ingredients or miniature pellets or liquid. These are made in two halves: a smaller-diameter "body" that is filled and then sealed using a larger-diameter "cap." Capsules can be made from aqueous solutions of gelling agents such as animal protein (gelatin) or plant polysaccharides or their derivatives (carrageenan, modified starch, cellulose). Other ingredients can be added to the gelling agent solution including plasticizers such as glycerin or sorbitol to decrease the capsule's hardness, colors, preservatives, disintegrants, and lubricants.

The composition can also include additional hard-shelled capsules mixed with the substantially spherical granules. Hard gelatin capsule shells can be produced by dipping of pins or pegs on a metal plate of the desired shape and diameter into a reservoir of the melted gelatin mixture. The pegs are made of manganese bronze. As the plate is lowered to the gelatin bath, the pegs are submerged to the desired depth. The desired thickness of coating is achieved by controlling the time of coating. After the plates and pegs are lifted from the gelatin bath, the gelatin on the pegs is dried by flowing air with controlled temperature and humidity. Once dried, each capsule part is trimmed to the proper length and removed from the pegs. It is important to control the thickness of the gelatin walls, since it affects the snugness of the fit between the capsule body and cap. Capsule shells can be manufactured in various sizes, lengths, diameters, and capacities.

The composition can therefore include any or all of the following substances in a mixture with the substantially spherical granules: micro-encapsulated substances, macro-encapsulated substances, and therapeutic components. These can be included, along with the substantially spherical granules, in a carrier. A skilled artisan can specifically select which components can be used based upon the specific usage.

The composition can further include strontium phosphate and iron (II) phosphate. The composition can also further include at least one selected from sodium phosphate dibasic ($Na_2HPO_4$) and sodium phosphate monobasic ($NaH_2PO_4$).

The present disclosure also contemplates a method of producing the composition including the substantially spherical granules. The method can generally include a step of providing a mixture of a biological active powder, magnesium phosphate, and an initiator with a colloidal silica solution, as described in greater detail hereinabove. The initiator can include one of MgO, CaO, and $K_2O$.

It should be appreciated that when magnesium phosphate powder is mixed in colloidal $SiO_2$ aqueous solution, followed by subjecting into dual centrifugation, not only can the three components be formed into spherical granules, any powder around them will also be encapsulated and be part of the spherical granules. This method enables the creation of bioactive spherical granules with various synergetic compositions. Under asymmetric centrifugation, magnesium phosphate and silica can have interactions resulting in formation of spherical granules in sizes ranging from about 0.25 mm to about 4 mm. The particles of magnesium phosphate can be in tens of micron meters range. After the combination of these small particles along with silica nanoparticles, the surfaces of the spherical granules are highly rough and filled with many micropores in the sizes of a few to hundreds of nanometers, the advantages of which are described herein.

The method can include a step of rotating mixture with dual asymmetric centrifugation (DAC) for a predetermined amount of time. The DAC process is a kinetic consolidation, milling, and polishing process wherein DAC speeds can be varied for discrete periods of time while the contents of the mixing vessel undergo an acid/base neutralization reaction. The interaction between the independent input variables (e.g., phase composition of the reactants, % crystal water, mixing rpm per step, number of mixing steps, time per step, total elapsed time, etc.) can affect the output variables, such as particle size and mechanical strength, and can therefore be used to controllably produce particles having desired properties. One of skill in the art can adjust these variables to create a specific granule size and configuration as required for an intended use.

The use of high rpm (>1000) can be important during the initial stages of DAC manufacturing for reactant mixing, and particle formation/consolidation. A high rpm facilitates both instantaneous mixing of the reactants and concurrent consolidation of particles during the acid/base reaction resulting from the mixing. High rpm during the initial stages of manufacturing results in a population of substantially spherical particles (weighted towards the upper limit of 25 µm-3 mm) with considerable mechanical properties (relative to particles produced using low rpm during the mixing and consolidation steps).

The use of a low rpm (<1000) can be important for milling and polishing of the formed particles in the DAC manufacturing process once the particles have been formed. DAC processing of the particles under a low rpm reduces the particle size distribution and polishes the surfaces of the particles to eliminate defects. Thus, in some embodiments, one or more high rpm DAC steps are conducted followed by one or more low rpm DAC steps. In one particular embodiment, the centrifugation of the rotating step can be performed at 800-1900 revolutions per minute, and the predetermined amount of time can be from about 20 seconds to about 2 minutes.

Suitable commercially available centrifugal mixer DAC systems include, but are not limited to, Flacktek SpeedMixers®, which include DAC 150 Series mixers, the DAC 250 Mixers, the DAC 400 Mixers, the DAC 600 Mixers, the DAC 800 Mixers, the DAC 1100 Mixers, DAC 3000 HP mixers, and DAC 5000 HP mixers. Commercially available DAC systems are generally sold in size ranges capable of processing samples from 100 g-10 kg. Various containers, including certain polypropylene jars, are specifically designed for use with DAC, and can be used to mix any additives with the reaction mixture prior to dual asymmetric centrifugation. The total amount of contents within the DAC jar is a variable that is important for efficient mixing and should be properly calibrated to the jar size and axes of rotation for optimal results. If the center of mass of the jar contents sits at or above the center of the flow diagram, then the contents will be accelerated out of the flow pattern (typically against the lid of the jar) and will not be dispersed within the paste. One of skill in the art can select the appropriately sized jar to create the appropriate granules.

In certain embodiments, spherical particles of dicalcium phosphate ($CaHPO_4$), $MgHPO_4 \cdot 3H_2O$ and $SiO_2$ can be produced with DAC process. While bound to no particular theory, it is believed that the interactions between $MgHPO_4 \cdot 3H_2O$, MgO and colloidal $SiO_2$ solution play a crucial role for the formation of the substantially spherical particles during DAC process.

In certain embodiments, a powder of bioactive glass/calcium phosphate, $MgHPO_4 \cdot 3H_2O$ and MgO are mixed with colloidal $SiO_2$ solution in a closed plastic jar. Alternatively, the colloidal $SiO_2$ solution can be diluted with deionized $H_2O$ in the closed plastic jar. In either case, the mixture can then be subjected to a series of DAC steps. The steps can start at high rpm (>1000 rpm) and can be lowered to low rpm (<800 rpm) at later steps. Spherical granules are obtained.

In certain embodiments, a powder of bioactive glass/calcium phosphate, $MgHPO_4 \cdot 3H_2O$ and MgO are mixed with colloidal $SiO_2$ solution in a closed plastic jar. Alternatively, the colloidal $SiO_2$ solution can be diluted with deionized $H_2O$ in the closed plastic jar. In either case, the mixture is then subjected to a series of DAC steps. The steps can start at low rpm (<800 rpm). A hardened mass is obtained, followed by granulation process into granules. The granulation can be achieved by carefully breaking the hardened mass into pieces until the desirable sizes are reached. The granulation can also be automated with proper machinery, such as a granulator.

In certain embodiments, a powder of bioactive glass/calcium phosphate, $MgHPO_4 \cdot 3H_2O$ and $MgO$ can mixed with colloidal $SiO_2$ solution in a specially shaped mold. Alternatively, the colloidal $SiO_2$ solution can be diluted with deionized $H_2O$ in the closed plastic jar. In either case, the mixture can then be left to set either under ambient or heating process to form a hard block.

In certain embodiments, powder of bioactive glass/calcium phosphate, $Na_2B_2O_4 \cdot 10H_2O$, $MgHPO_4 \cdot 3H_2O$ and $MgO$ are mixed with colloidal $SiO_2$ solution to form a paste. The paste then becomes injectable through thin opening such as a needle or a cannula. This paste can slowly set into a hard block. In certain embodiments, the spherical granules made with $MgHPO_4 \cdot 3H_2O$, and nano silica can be selected based on the diameters to obtain small spheres between 0.1 mm and 0.5 mm. These small granules can be mixed with the injectable paste. The paste can hold onto the surfaces of the small granules so that the paste does not leak through fine cracks inside bony defects easily under mechanical load.

The method can include a step of drying the resulting material from the rotating step. The drying step can include an evaporation process under an environment selected from ambient air, pressurized flow of air, ambient inert gas, and pressurized flow of inert gas. (e.g., nitrogen, argon). The drying step can include an evaporation process under vacuum conditions. The drying step can include an evaporation process via repeatedly washing with a solvent with low vapor pressure (e.g., methanol, ethanol, acetone, propanol, hexane). The drying step can include an evaporation process via a heating process using heating equipment, such as a conventional oven, a culture incubator or a microwave oven.

While the different examples herein describe the formulations having Ca and Mg phosphate phases as the predominant components, other alkaline earth metals such as Strontium (Sr) and Iron (Fe) can be added without departing from the spirit of the invention. For example, the composition can include one of strontium phosphate and Iron (II) phosphate.

It is also contemplated that compositions containing the substantially spherical particles can be made available to practitioners such as surgeons, veterinarians, or dentists via a kit containing one or more key components. A non-limiting example of such a kit includes dry (e.g., a powder containing the substantially spherical particles) and liquid components in separate containers, where the containers can or cannot be present in a combined configuration. Many other kits are possible, such as kits comprising a pre-mixed putty instead of the powder and setting solution, and kits including a syringe or multiple syringes for injecting a bone cement composition formed from the components of such kit. The kits typically further include instructions for using the components of the kit to practice the subject methods. The instructions for practicing the subject methods are generally recorded on a suitable recording medium. For example, the instructions can be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example embodiments of the present technology are provided with reference to the several figures enclosed herewith.

Example 1

Figure 1:
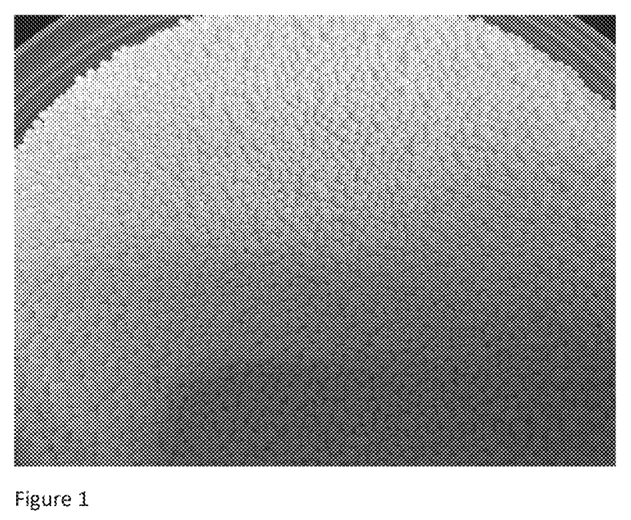
FIG. 1 illustrates substantially spherical granules including magnesium phosphate, silica, and calcium phosphate.
Figure 2:
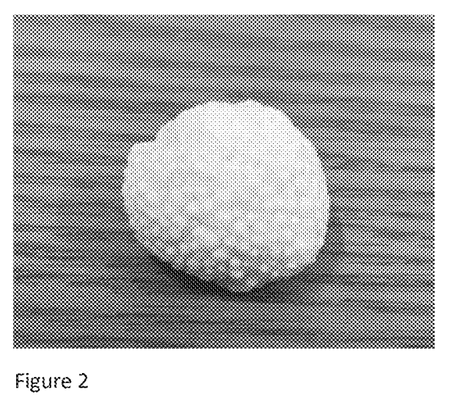
FIG. 2 illustrates putty including spherical granules and hydrated cellulose polymer.

The dry powder components 110.4 g $Ca(OH)_2$ and 27.6 g $Mg(OH)_2$ were mixed with the liquid component $H_3PO_4$ (156 ml) diluted with 204 ml of $H_2O$ and 24 g of sodium bicarbonate in a reaction vessel using a mixer. The resulting slurry was dehydrated using an oven to form a dry cake. The cake was then milled to create a fine powder which was collected using stainless steel mesh sieves. The dried fine CaP+MgP powder (containing a mixture of Monetite and newberyite) was added to an empty plastic jar. 8.75 g of Magnesium oxide (MgO) powder was added to the beaker and the resulting dry powder mixture (containing CaP, MgP, and MgO) was homogenized. A solution comprising colloidal silica and ultrapure deionized water was prepared in another plastic jar. The dry powder mixture was added to the jar containing the silica solution. It underwent a centrifugation process leading to formation of granules or substantially spherical beads as seen in FIG. 1. Immediately following granulation, the particles were dehydrated using an oven. With the use of a polymeric carrier (Sodium CMC), handling properties of the beads were improved. Upon hydration, this carrier swells and forms a putty as seen in FIG. 2.

Figure 3:
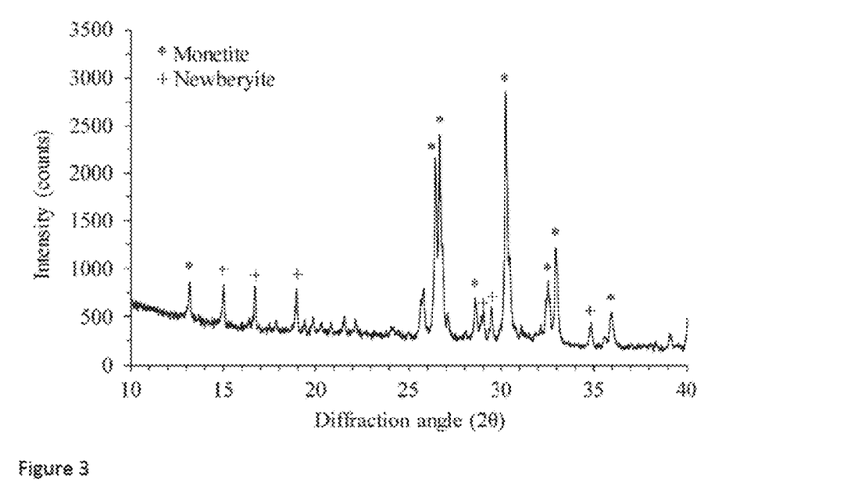
FIG. 3 is a PXRD pattern collected from spherical granules including magnesium phosphate, silica, and calcium phosphate.
Figure 4:
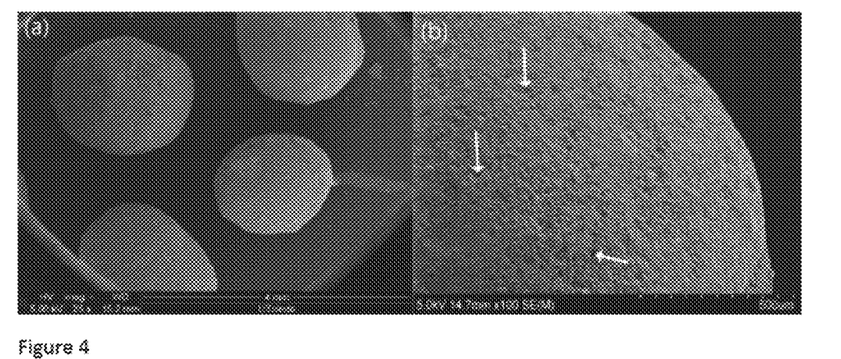
FIGS. 4a-4b include SEM images of (a) spherical granules between 1 mm and 2 mm including magnesium phosphate, silica, and calcium phosphate, (b) the surface of the granule, with arrows showing surface pores.

FIG. 3 is a PXRD pattern from these SiMN granules showing 2 distinct crystalline phases: Monetite indicated by * and Newberyite indicated by +. The formed granules had a porous surface as seen in SEM images in FIGS. 4-5. FIG. 4a showed typical morphology of SiMN granules. The diameters of these granules are between 1 mm and 2 mm. At higher magnifications, highly rough surfaces of granule were revealed. Numerous micro-pores can be observed across the surface of a granule (arrows in 4b). The rough surfaces are formed by bonding of particles of monetite, newberyite and silica.

Figure 5:
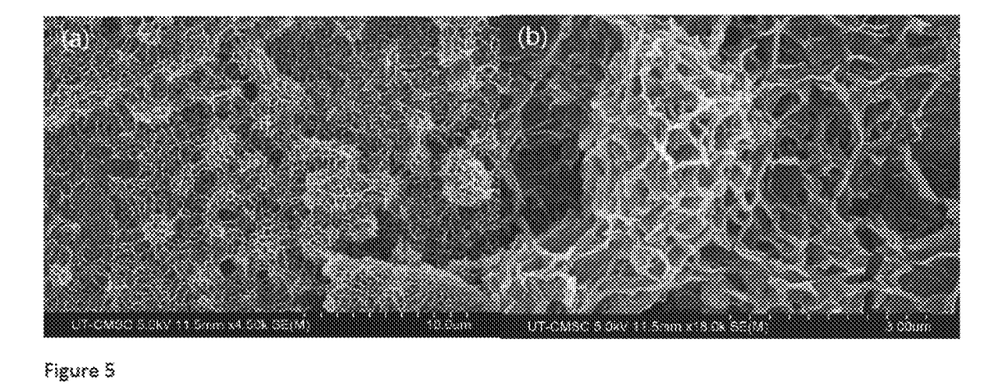
FIGS. 5a-5b include SEM images of the surface of mixture comprising magnesium phosphate, silica, and calcium phosphate: (a) cauliflower-like globules and (b) the globules including of many platelet particles.
Figure 6:
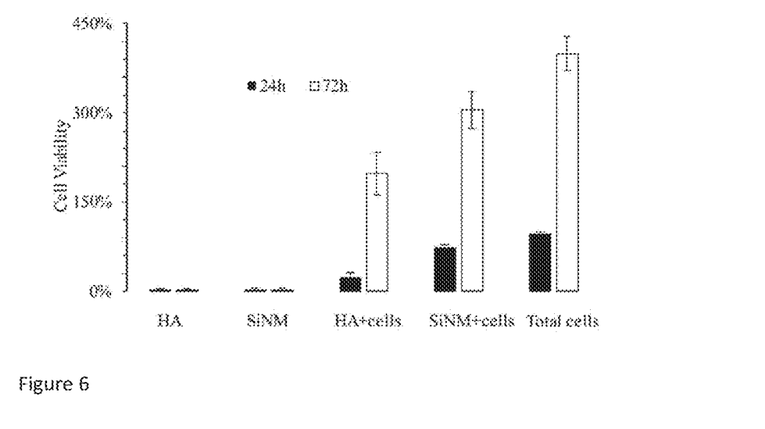
FIG. 6 is a graph describing attachment and proliferation of MC3T3-E1 cells in the presence of a mixture comprising magnesium phosphate, silica, and calcium phosphate.

The granules are bioactive as seen from FIG. 5. After soaking in the Tas-simulated body fluid (t-SBF) for 2 days, an additional layer was observed on the surface of granules as shown FIG. 5a. This layer had many cauliflower-like globules with an average size of about 5 μm. At higher magnification, the shape of the crystals that form globules was revealed as platelets (FIG. 5b). There was no additional particle observed on the negative control, polyethylene, suggesting the solution does not promote any crystal growth on the surface of a given substrate. As shown in FIG. 6, the positive control represented the total amount of seeded cells in the media, and about 25% of cells attached to the HA control after 24 hours and increased to 50% after 72 hours. On the other hand, 75% of seeded cells attached to the disclosed composition after 24 hours. The quantity of cells attached on the disclosed composition showed a 4-fold increase and remained 75% of the total after 72 hours of culturing.

All μCT images revealed well-placed defects with no evidence of infection or adverse reaction to the implanted materials based on radiographic appearance of the adjacent host bone in the defects at 6 or 12 weeks. Representative μCT images are presented in FIG. 7 at 500 μm thickness in coronal plane.

Figure 7:
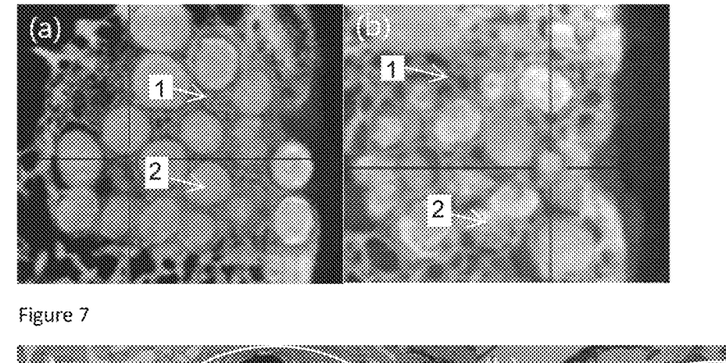
FIG. 7 is images of micro-CT scans (500 µm thickness) in the coronal plane of (a) and (b) spherical granules including magnesium phosphate, silica and calcium phosphate.
Figure 8:
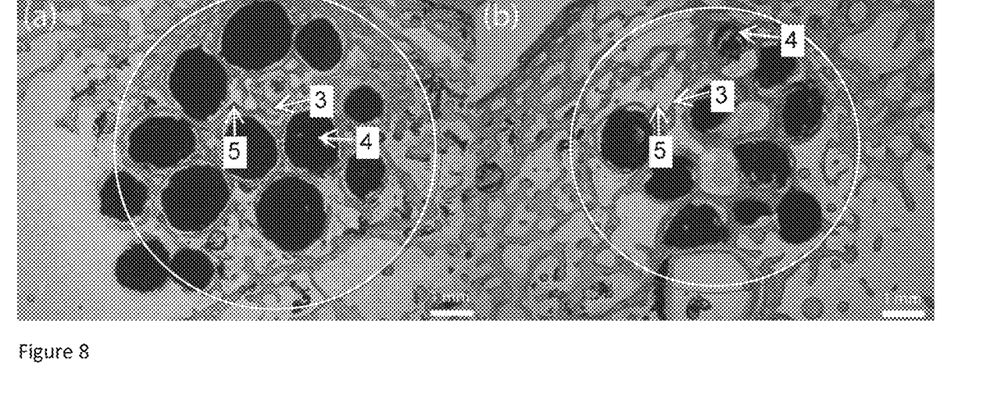
FIGS. 8a-8b are low magnification representative histological images of spherical granules including magnesium phosphate, silica and calcium in rabbit distal femoral condyle, respectively, showing highly regular new bone infiltration into the center of the spherical granules; arrow 4 indicates graft material, while arrow 3 show new bone tissues, arrow 5 shows the bone marrow and the circle indicates the surgically created defect.

In images of μCT taken at 6 weeks, new bone formations were observed among the spherical granules. The new bone had completely penetrated the packed granules and was present both in the center and at the margins of the defect (FIG. 7, arrow 1). The spherical geometry of the granules observed at the 6 weeks was lost by 12 weeks with loss of details at the edges due to graft remodeling (FIGS. 7a and 7b, arrow 2). The new bone formations in the defects had remodeled from 6 to 12 weeks. The dense thin trabecular formations (FIG. 8a, arrow 3) observed at 6 weeks had matured into well-organized thicker trabeculae (FIG. 8b, arrow 3).

No adverse reactions in terms of inflammatory cellular response were noted at 6 weeks. Newly formed bone was found on both graft materials from the margins through the center of the defects at 6 weeks (bone indicated by arrow 3 in FIG. 8a). At 12 weeks, development of marrow cavities and bone remodeling was observed for both groups as shown with arrow 5 in FIG. 8(b). Resorption of the spherical granules was observed as an erosion of characteristic circular shape and formation of cavities within the granules (arrow 4, FIG. 8b). Furthermore, the new bone formed in the defects had higher aspect ratio, with longer and thinner trabeculae as indicated at arrow 3 in FIGS. 8a and 8b. It can be observed here that the infiltration of new bone was highly regular among the spherical granules, due to the substantially isotropic geometry of the granules.

Figure 9:
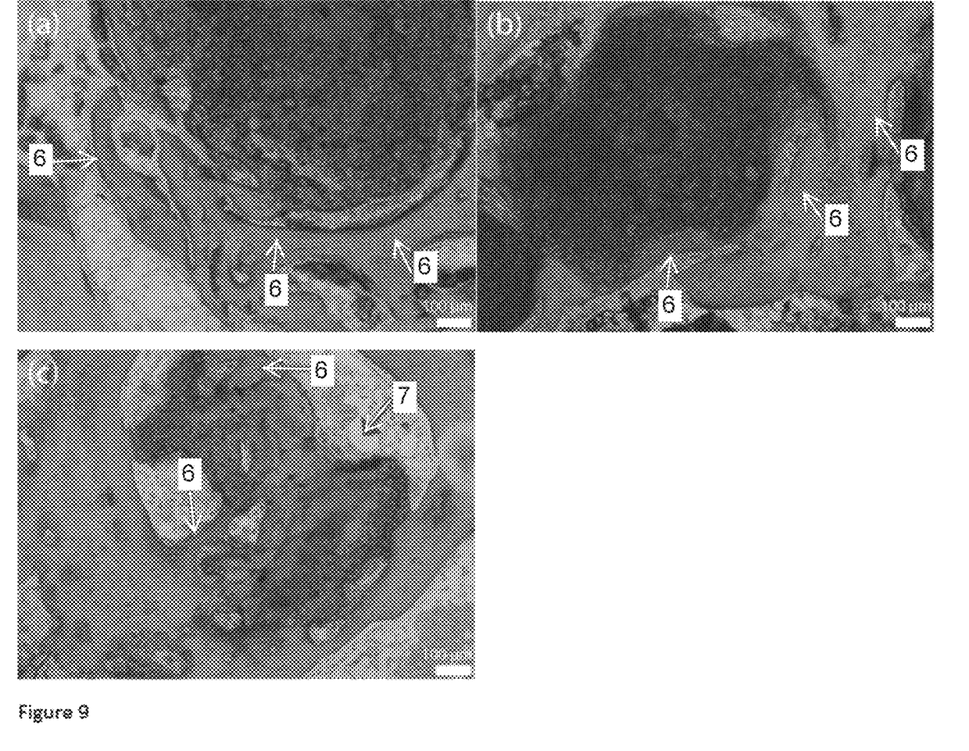
FIGS. 9a-9c include high magnification histology images of the interface between new bone and spherical granules including magnesium phosphate, silica and calcium phosphate, surrounded by marrow (arrow 7) and new bone on the surface of the residual particle (arrow 6), showing the penetration of new bone into the spherical granule.

At higher magnifications, as shown in FIG. 9, the orientation of fibers within the new bone can be visualized. The bone grown around surfaces of the spherical granules at 6 weeks exhibited an organized orientation at areas close to the bone surface, following the granule surface and stacking layer by layer in perpendicular axis indicating a lamellar structure (FIG. 9a, arrow 6). The same structure was observed at 12 weeks, too (FIG. 9b, arrow 6).

An intriguing observation was also found at the interfaces between SiMN graft and new bone. The spherical graft showed dynamic integration with the new bone, as the graft volume shrank due to resorption. At 12 weeks, the continuous bone growth matching graft resorption profile can be observed more clearly. As shown in FIG. 9c, more than half of the granule had been resorbed at 12 weeks, and the remnant were encapsulated by marrow cavity and a piece of bone grown in circle, which most likely matched the original shape of this granule before any resorption happened. At multiple sites, focal bone formations were observed bridging onto the graft (arrow 7), leading to encapsulation of the remnant with another layer of bone. The fact that new bone directly infiltrated into the very center of the granule without full resorption of the granule indicated that the micropores existed in the granules most likely can expand upon degradation and allows the further degradation of the granules to happen from their inside, instead of eroding gradually from the outside.

Example 2

Formulation with Bioglass

Spherical granules were made by mixing the solid components comprised of 118 g of Bioglass, 79 g of Magnesium phosphate powder and 8.75 g of Magnesium oxide (MgO) with the liquid component consisting of 42 ml of Colloidal Silica solution (HS-40 Silica) and 63 ml of water. This mixture was then subjected to the centrifugation method described in Example 1. The centrifugation was a series of different rpm conditions starting with higher number and moving to a lower number. Immediately following granulation, the particles were dehydrated using an oven.

Example 3

Addition of Antibiotic

The solid phase (powder) of the spherical granules was blended with 10% w/w vancomycin (VCM), an antibiotic effective against methicillin resistant Staphylococcus aureus (MRSA), and 10% w/w sodium CMC mixed with double-distilled water to form a paste was molded into 0.1-g pellets and air dried. These pellets were immersed individually in 1 mL of phosphate-buffered saline at 37° C. The amount of vancomycin released was measured by ultraviolet/visible spectroscopy at 280 nm at different time points, and the concentration was calculated using a standard curve of absorbance vs. concentration.

Figure 10:
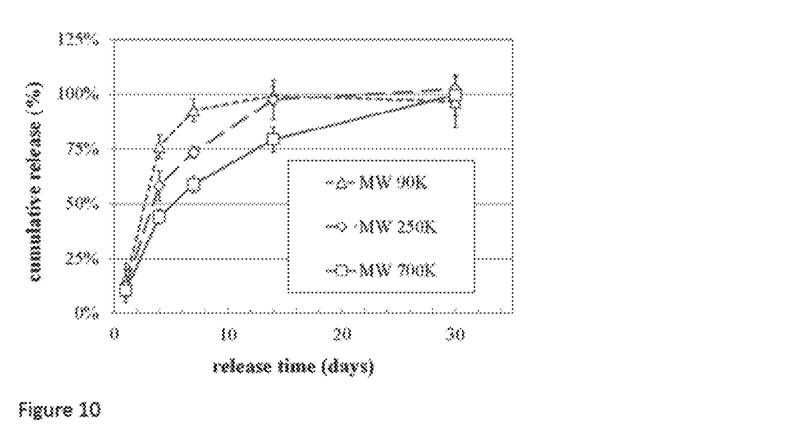
FIG. 10 is a graph illustrating vancomycin (VCM) release profiles when mixing with spherical granules including magnesium phosphate, calcium phosphate, silica, and different biopolymers over 1, 4, 7, 14, or 30 days. The biopolymer is sodium carboxymethyl cellulose with molecular weight of 90,000, 250,000, or 700,000 Da.

We investigated CPC containing CMC of various chain lengths, expressed in terms of the molecular weight (90,000, 250,000, or 700,000 Da). The results indicated that adding high-molecular-weight (700,000 Da) CMC retarded drug release from CPC (FIG. 10), suggesting a critical factor affecting this drug delivery system.

Example 4

MgP Formulation with or without Granules

A flowable cement, made by mixing Magnesium phosphate, Magnesium oxide (MgO), Colloidal $SiO_2$ solution and sodium tetraborate (Borax™) can be mixed with the small substantially spherical SiMN granules (with the diameter between 250-750 micrometers), made by a method described in Example 1. This formulation results in flowable cement with microbeads suspended uniformly throughout. This flowable cement can also be used as a standalone injectable cement which will slowly set into hardened mass.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments can be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A composition for bone regeneration, the composition comprising:
   substantially spherical granules, each of the spherical granules including:
   an outer shell including magnesium phosphate and nano-sized silica;
   a bioactive core encapsulated by the outer shell, the bioactive core including at least one of:

calcium phosphate including hydroxyapatite (HA) and β-tricalcium phosphate (β-TCP), the HA and β-TCP combined at a predetermined ratio ranging between 60:40 to 10:90 and configured to balance the bioactive nature of β-TCP and the stability of the HA, and bioactive glass, wherein the granules include macro-pores and micro-pores, the macro-pores being intergranular spaces between adjacent granules, and the micro-pores being intragranular nanopores formed on the outer shell of each of the granules, and wherein the bioactive core includes at least one of sodium phosphate dibasic ($Na_2HPO_4$) and sodium phosphate monobasic ($NaH_2PO_4$).

2. The composition of claim 1, wherein the bioactive glass includes at least one of 45S5, S53P4, 13-93, 58S, 68S, 63S, 77S, 80S, 35SM, 85S, and 70S30C.

3. The composition of claim 1, wherein the magnesium phosphate includes at least one of $MgHPO_4$, $MgHPO_4 \cdot xH_2O$, $Mg_3(PO_4)_2$, and $Mg_3(PO_4)_2 \cdot xH_2O$.

4. The composition of claim 1, further including at least one selected from strontium phosphate and iron (II) phosphate.

5. A hydrogel including the composition of claim 1.

6. The hydrogel of claim 5, further including at least one of a biopolymer, a protein, a gums a carbohydrate, and a cellulose.

7. The hydrogel of claim 5, further including at least one therapeutic component.

8. The hydrogel of claim 7, wherein the therapeutic component includes at least one of vancomycin, tobramycin, or gentamycin.

9. A composition for bone regeneration, the composition comprising:

substantially spherical granules, each of the spherical granules including:

an outer shell including magnesium phosphate and nano-sized silica, the magnesium phosphate includes at least one of $MgHPO_4$, $MgHPO_4 \cdot xH_2O$, $Mg_3(PO_4)_2$, and $Mg_3(PO_4)_2 \cdot xH_2O$, a bioactive core encapsulated by the outer shell, bioactive core including at least one of calcium phosphate and bioactive glass, the calcium phosphate including hydroxyapatite (HA) and β-tricalcium phosphate (β-TCP), the HA and β-TCP combined at a predetermined ratio ranging between 60:40 to 10:90 and configured to balance the bioactive nature of β-TCP and the stability of the HA, the bioactive glass including at least one of 45S5, S53P4, 13-93, 58S, 68S, 63S, 77S, 80S, 35SM, 85S, and 70S30C, at least one selected from strontium phosphate and iron (II) phosphate, and wherein the granules include macro-pores and micro-pores, the macro-pores being intergranular spaces between adjacent granules, and the micro-pores being intragranular nanopores formed on the outer shell of each of the granules, and wherein the bioactive core includes at least one of sodium phosphate dibasic ($Na_2HPO_4$) and sodium phosphate monobasic ($NaH_2PO_4$).

* * * * *